(12) United States Patent
Sköld et al.

(10) Patent No.: US 9,017,964 B2
(45) Date of Patent: Apr. 28, 2015

(54) PREPARING BIOLOGICAL SAMPLES FOR ANALYSIS

(75) Inventors: Karl Sköld, Uppsala (SE); Marcus Svensson, Uppsala (SE); Göran Palmers, Askim (SE); Per Andrén, Uppsala (SE)

(73) Assignee: Denator Aktiebolag, Gothenburg (SE)

( * ) Notice: Subject to any disclaimer, the term of this patent is extended or adjusted under 35 U.S.C. 154(b) by 1642 days.

(21) Appl. No.: 11/996,545

(22) PCT Filed: Aug. 27, 2006

(86) PCT No.: PCT/SE2006/000979
§ 371 (c)(1),
(2), (4) Date: Jun. 25, 2008

(87) PCT Pub. No.: WO2007/024185
PCT Pub. Date: Mar. 1, 2007

(65) Prior Publication Data
US 2008/0268495 A1     Oct. 30, 2008

Related U.S. Application Data

(63) Continuation-in-part of application No. 11/212,454, filed on Aug. 26, 2005, now abandoned.

(51) Int. Cl.
*G01N 1/44* (2006.01)
*G01N 1/28* (2006.01)
*G01N 33/68* (2006.01)
*C07K 14/435* (2006.01)

(52) U.S. Cl.
CPC *G01N 1/44* (2013.01); *G01N 33/68* (2013.01); *G01N 1/286* (2013.01); *B01J 2219/00051* (2013.01); *C07K 14/435* (2013.01)

(58) Field of Classification Search
None
See application file for complete search history.

(56) References Cited

U.S. PATENT DOCUMENTS 4,891,239 A    1/1990    Dudley

FOREIGN PATENT DOCUMENTS

EP    1442794 A2    8/2004

OTHER PUBLICATIONS

TA Instruments "Differential Scanning Calorimetry (DSC)" TA Instruments, Jun. 11, 1997, retrieved online from <URL:www1.chm.colostate.edu/Files/CIFDSC/dsc2000.pdfSimilar>, 96 pages.*
Wang, N.M, Experiment No. 8B: Aseptic Culture Techniques Petri Dish Preparation, archived online Nov. 5, 2002, <URL:http://www.eng.umd.edu/~nsw/ench485/lab8b.htm>, retrieved Dec. 15, 2011, 6 pages.*

(Continued)

*Primary Examiner* — Jon P Weber
*Assistant Examiner* — Aaron J Kosar
(74) *Attorney, Agent, or Firm* — Dentons US LLP (57) ABSTRACT

Methods and devices for preparing a biological sample for analysis are described. The biological sample from an organism has at least one macromolecule having a primary structure that naturally degrades after the sample is removed from the organism. The method includes causing the biological sample to adopt a shape to permit rapid and uniform heating. The shaped sample is then rapidly and uniformly heated, thereby altering a secondary structure of the macromolecule while preserving its primary structure.

10 Claims, 5 Drawing Sheets

(56) References Cited

OTHER PUBLICATIONS

Conservation Physics "An experimental chamber for generating a water vapour flux" Conservation physics.org, <URL: http://www.conservationphysics.org/mudbuf/fluxgen.php>, Feb. 1, 2001 (retrieved Jun. 15, 2014), 2 pages.*

Agilent Technologies, Accessories and Supplies for UV-Visible Spectroscopy, Mar. 1, 2002, pub No. 5988-5967EN, 36 pages.*

International Search Report for PCT/SE2006/0009797, Dec. 6, 2006, 5 pages.

Che Fa-Yun, et. al., "Quantitative Neuropeptidomics of Microwaveirradiated Mouse Brain and Pituitary", Molecular & Cellular Proteomics 4.9, Jun. 21, 2005, vol. 4, p. 1391-1405.

Robinson Martin P., "Electromagnetic re-warming of cryopreserved tissues: effect of choice of cryoprotectant and sample shape on uniformity of heating", Phys. Med. Biol. 2002, vol. 47, p. 2311-2325.

Svensson Marcus, et. al., "Peptidomics-Based Discovery of Noel Neuropeptides", Journal of Proteome Research 2003, vol. 2, p. 213-219.

Theodorsson Elvar, et. al., "Microwave Irradiation Increases Recovery of Neuropeptides from Brain Tissue", Peptides 1990, vol. 11, p. 1191-1197.

Aleksander A. Mathe, "Neuropeptides in Brain: Effects of Microwave Irradiation and Decapitation," Life Sciences, Nov. 28, 1989, vol. 46, pp. 287-293.

Meyerhoff, James L., "Increase in Dopamine in Cerebral Cortex and Other Regions of Rat Brain After Microwave Fixation," Brain Research, Jan. 1, 1978, vol. 152, pp. 161-169.

Nylander, I., "A Comparison Between Microwave Irradiation and Decapitation," Neuropeptides, May 31, 1997, vol. 31. pp. 357-365.

O'Callaghan, James P., "Focused Microwave Irradiation of the Brain Preserves in Vivo Protein Phosphorylation," Dec. 16, 2003, Jrnl. of Neuroscience Mthds., vol. 135, pp. 159-168.

Skold, Karl, "A Neuroproteomic Approach to Targeting Neuropeptides in the Brain," Nov. 18, 2001, Prtoeomics 2002, vol. 2, pp. 447-454.

* cited by examiner

PREPARING BIOLOGICAL SAMPLES FOR ANALYSIS

CLAIM OF PRIORITY

This application is a continuation-in-part of, and claims the benefit of priority under 35 U.S.C. § 120 to, U.S. patent application Ser. No. 11/212,454, filed Aug. 26, 2005 now abandoned, which is incorporated herein by reference in its entirety.

TECHNICAL FIELD

The present invention relates to methods and apparatus for preparing a biological sample for analysis. The invention more particularly relates to methods and apparatus for heating a biological sample soon after it is extracted so that the primary structures of proteins in it are not degraded.

BACKGROUND

It is key to any analysis of a biological sample that the integrity of its constituents is conserved between the time that the sample is extracted from a living organism and the time that analysis is carried out. Sample degradation, however, is both hard to impede, and hard to detect. The result is that many analyses miss the presence of species that have degraded long before the analysis is carried out; correspondingly, such analyses may in fact identify degradation products of critical components in place of the original components.

Since the sequencing of the human genome and the realization that there may be far fewer genes than was originally thought, attention has turned to the proteome; it is now believed that it is the assemblage of proteins in an organism that is the key to understanding physiology, disease, and function. Proteins are found in many different environments, for example, in cell nuclei, organelles, protoplasm, and membranes, as well as the inter-cellular space, and in body fluids such as blood. Despite their ubiquity, proteins are extremely sensitive to their environments and thus are not always easy to detect and to identify because they can degrade very quickly.

A protein is composed of one or more strings (polypeptide chains) of the residues of the 20 naturally occurring amino acids, which fold into specific 2- and 3-dimensional structures that determine the protein's activity. A given protein has a unique sequence of amino acids, termed its primary structure. The secondary structure is defined by dihedral angles (referred to as phi and psi) of the backbone atoms of the amino acid residues, and the hydrogen bonds between side chain and backbone atoms. The dihedral angles and patterns of hydrogen bonds within certain characteristic subsequences of consecutive (and non-consecutive) residues, can give rise to units of secondary structure that are relatively stable, e.g., so-called alpha helices, and beta sheets.

The tertiary structure of a protein is the term used to refer to how the secondary structure units and the polypeptide chains that connect them fold into a three dimensional structure. The quaternary structure refers to how two or more non-contiguous polypeptide chains that each adopt their own tertiary structure also associate with one another to form a protein. A protein's function may derive from either or both of its tertiary and quaternary structure. Typically the three-dimensional conformations adopted by the one or more polypeptide chains give rise to features, often described as clefts, cavities, or grooves depending on their geometry, that can bind to other molecules with high specificity. Such other molecules include drugs, nucleic acids, and most significantly for sample integrity, other proteins and polypeptides.

The natural functions of the assemblage of proteins in an organism are kept in check by a complex but delicate balance of biochemical pathways while the organism is alive. Once an organism dies, or once a sample of tissue is extracted from a living organism, the regulatory balance of the organism or in the sample is lost and key proteins start to break down. The breakdown can manifest itself in a number of different ways. For example, some proteins whose natural role is to digest other proteins (a "proteolytic" function), and whose natural levels are kept in check while an organism is alive, may go out of control after death. Thus, many proteins and key polypeptides such as coactivators, hormones, and corepressors, end up being actually digested by naturally occurring proteolytic proteins in the sample. Digestion typically involves a rupturing of the polypeptide backbone at one or more points, thereby resulting in protein or peptide fragments. Still other proteins may naturally decompose by other means, such as hydrolysis; whereas in a living organism their levels are maintained because they are continually synthesized, after death they rapidly disappear. For example, post-mortem activity of proteases and oxidative stress has been shown to play an important role on peptide and protein concentration in the brain, as well as for detecting post-translational modifications (K. Sköld et al., "A Neuroproteomoic Approach to Targeting Neuropeptides in the Brain", *Proteomics*, 2, 447-454, (2002); M. Svensson et al., "Peptidomics-Based Discovery of Novel Neuropeptides", *J. Proteome Res.*, 2, 213-219, (2003), both of which are incorporated herein by reference.

For purposes of protein identification, however, to determine what proteins are present in a sample, it is sufficient to be able to ascertain their respective primary structures, i.e., sequences. Proteins and polypeptides have been widely investigated by methods such as two dimensional gels and mass spectrometry, but such techniques depend on having access to samples in which natural protein degradation has not advanced to a point where the concentrations of critical species have been reduced below the various measurement thresholds.

To study proteins and peptides, tissue or cell samples are usually disrupted by homogenization in certain specific buffer conditions. These buffers often contain ingredients that are supposed to cause a cessation of all protein activity, including proteins (proteases) that degrade other proteins. However, the study of tissue samples from patients or model organisms usually exposes the samples to a certain period of oxygen and nutrient depletion before homogenization and protease inactivation occurs.

Consequently, techniques have been developed in the art for attempting to preserve biological samples after extraction and prior to analysis. Examples of such techniques include tissue fixation, which typically involves immersing a sample in an aldehyde solution, and irradiating samples with microwaves (see, e.g., Theodorsson, et al., "Microwave Irradiation Increases Recovery of Neuropeptides From Brain Tissues", *Peptides*, 11:1191-1197, (1990)). Use of aldehyde solutions is problematic because it doesn't arrest natural degradation of proteins (though it is somewhat effective at maintaining large-scale structure of tissues). Microwave irradiation is problematic because it is generally non-uniform, that is, some parts of the sample reach a temperature that is high enough to cause sample breakdown. (See, for example, Fricker et al., "Quantitative Neuropeptidomics of Microwave-irradiated Mouse Brain and Pituitary", *Molecular & Cellular Proteomics*, 4:1391-1405, (2005).) Furthermore, microwave irradiation has formerly been applied to living (non-human) subjects as part of a sacrificial protocol and thus has yet to be established as a tool for analyzing samples that have been extracted from subjects, both human and non-human.

Accordingly, there is a need for a reliable technique for preserving the contents of tissue samples prior to analysis in a way that impedes natural degradation and that acts on a given sample reliably.

The discussion of the background to the invention herein is included to explain the context of the invention. This is not to be taken as an admission that any of the material referred to was published, known, or part of the common general knowledge as at the priority date of any of the claims.

Throughout the description and claims of the specification the word "comprise" and variations thereof, such as "comprising" and "comprises", is not intended to exclude other additives, components, integers or steps.

SUMMARY

The present invention comprises a method for preparing a biological sample for analysis. The biological sample comprises at least one protein or polypeptide, having an amino acid sequence, from an organism. The method comprises causing a volume of the sample to adopt a shape wherein the shape permits uniform and rapid heating, thereby forming a shaped sample; and heating the shaped sample so that the secondary structure of the macromolecule is disrupted, but the primary structure is not. In an embodiment, the biological sample is given a shape that facilitates an effective heating in terms of the heating being uniform and fast. This helps to shorten the time needed to reach a disrupted secondary structure. By blocking certain biological processes driven by proteins, degradation of other constituents of the sample is avoided. Because the time between taking the biological sample and performing a biological analysis has a large impact on the level of degradation, even after a short time, e.g., after as little as 1-3 minutes, it is important that heating takes place immediately after taking the sample. By heating the tissue proteins that function as proteases, their secondary and tertiary structure, and thereby their function, is lost.

The method preserves the primary structure of proteins and peptides but simultaneously disrupts their original secondary, tertiary structures, and, where applicable, quaternary structures. The heating of the sample therefore has several advantages, including enabling species such as the relatively low-abundant neuropeptides and proteins that would otherwise be digested to remain intact. In addition, the method minimizes degradation of neuropeptides and proteins in a reproducible manner. This method also makes it possible to compare the content and levels of proteins and peptides from different samples. Also, because a sample can be taken from an organism without sacrificing the entire organism, the method may be non-fatal, i.e., the organism does not have to perish as a consequence of using the method.

The present invention further includes a method for preparing a biological sample for analysis, the sample comprising at least one macromolecule having a primary structure and a secondary structure, the method comprising: causing a volume of the sample to adopt a shape wherein the shape permits uniform and rapid heating, thereby forming a shaped sample; and heating the shaped sample so that the secondary structure of the macromolecule is disrupted, but the primary structure is not, wherein the heating reduces proteolytic activity by at least 70%.

The present invention still further includes a method for preparing a biological sample for analysis, the sample comprising a proteolytic molecule and a polypeptide, wherein the polypeptide have a primary structure and secondary structure, the method comprising: heating the biological sample to cause the sample to uniformly attain a temperature at which the activity of the proteolytic molecule is disrupted enough so that the proteolytic molecule are unable to degrade the primary structure of the polypeptide.

The present invention also includes a method for preparing a biological sample from an organism for analysis, the sample comprising at least one macromolecule of interest, wherein the macromolecule of interest has a primary structure and a secondary structure, the method comprising: causing a volume of the sample to adopt a shape wherein the shape permits rapid and uniform heating, thereby creating a shaped sample; and heating the shaped sample to cause the shaped sample to attain a temperature wherein the temperature causes a secondary structure of a digestive molecule to degrade, wherein the digestive molecule naturally digests the macromolecule of interest when its secondary structure is intact, and wherein the temperature does not cause the primary structure of the macromolecule of interest to degrade.

The present invention even further includes a system for preparing a biological sample, the system comprising: a heat source; a retaining member in communication with the heat source, and configured to contact the biological sample, and wherein the retaining member conducts heat from the heat source into the biological sample; a zone in which the biological sample can be held at a controlled temperature; and a transfer element configured to move the biological sample out from the zone and onto the retaining member.

The present invention yet further includes a heating device, comprising: a chamber configured to receive a shaped biological sample, wherein the chamber has one or more internal surfaces that are in contact with the biological sample, and wherein the sample is totally contained within the chamber; one or more heating elements in communication with the one or more internal surfaces; a heat sensor in communication with the one or more internal surfaces; an inlet adapted to permit the sample to be directed into the chamber; and wherein the chamber has a shape so that no part of the sample is greater than 10 mm from a point on any one of the one or more internal surfaces.

The present invention additionally includes a fixed treated biological sample, comprising: a sample of biological material that has been extracted from an organism and that has a macromolecule which is not degraded, at least 60% of which has been denatured, per unit volume, as compared to the same macromolecule in the biological material in vivo.

DESCRIPTION OF DRAWINGS

Like reference symbols in the various drawings indicate like elements.

DETAILED DESCRIPTION

Overview

The present invention involves methods and apparatus for preparing a biological sample for analysis. The sample, which has been extracted from an organism, contains various macromolecules such as polypeptides or proteins. In order to prepare the sample for analysis, the natural degradation of the primary structures of the various macromolecules is arrested to the fullest extent possible.

Accordingly, in one embodiment, after a first period of time which is one over which degradation is minimal, or preferably kept at or around levels similar to those found in the sample when in vivo, the sample is caused to adopt a shape that permits rapid and uniform heating. Then, the sample is rapidly and uniformly heated over a second period of time, and in such a manner that all parts of the sample attain a particular temperature. The temperature is referred to as the denaturation temperature because it is a temperature at which various macromolecules denature, i.e., their secondary, tertiary, and/or quaternary structure is disrupted, but it is not a temperature at which the primary structure of the macromolecules is degraded. Preferably the macromolecules that are denatured include at least those macromolecules that play a role in the natural degradation processes of the sample. For example, such macromolecules include proteolytic enzymes that, if not denatured, would degrade—e.g., by digesting—other molecules in the sample.

It is to be understood that the conditions deployed herein lead to an effect of degree, rather than one that is absolute: it is of course understood that no chemical reaction can be halted altogether (save at the practically unattainable Absolute Zero of temperature). Thus, the effect of increasing (or decreasing) temperature, typically expressed mathematically by the exponential Arrhenius relationship, is one in which a statistically greater number of molecules react in a given way per second, as temperature is increased. Thus it is to be understood that, for example, although the temperatures employed are chosen to be high enough to cause denaturation, but low enough not to cause degradation of primary structure of a given set of molecules, it does not mean that a small number of those molecules do not still undergo degradation under those conditions. It is sufficient for the purposes of the present invention that the number of such molecules is insignificant and is, for example, less than 5% of the population of initial molecules, and is preferably less than 2%, and even more preferably less than 1%, and still more preferably less than 0.1% of the initial population of those molecules.

It is also to be understood that, when the term secondary structure is used herein, it can mean the overall three-dimensional configuration of a macromolecule that is responsible for its activity and specificity. Thus, the term secondary structure can mean, herein, features of a macromolecule that are commonly referred to distinctly as secondary, tertiary, and quaternary structure.

In a second embodiment, the sample is not intended to be analyzed soon after extraction but instead is intended to be stored prior to analysis. In such an embodiment, the sample is frozen as soon as is practically possible after extraction. The time between extraction and the time when the sample attains a frozen temperature is one over which degradation is minimal. The sample is caused to adopt a shape that permits rapid and uniform heating. The sample can also be caused to adopt such a shape while frozen, or prior to freezing. Then, the sample is rapidly and uniformly heated over a second period of time, and in such a manner that all parts of the sample attain the denaturation temperature. It is to be understood that the second period of time for a frozen sample is not necessarily the same as the second period of time for a sample that has not been frozen prior to heating. Preferably the second period of time is rapid so that the sample does not undergo a period of thawing in between its frozen state and the heated state. For example, rapid heating preferably occurs over less than a minute, less than 30 seconds, less than 20 seconds, less than 10 seconds, less than 5 seconds, or less than 2 seconds.

The present invention has contemplated application to analysis of polypeptides, proteins (including antibodies), carbohydrates, lipids, hormones, and metabolites in a biological sample. It would be understood, however, that study of other molecules and macromolecules may also benefit from the methods and apparatus described herein. For example, and in particular, any other macromolecules in a biological sample that have a three-dimensional conformation that may be disrupted by heating while preserving the sequence of chemical bonds within them can be preserved for analysis by the methods and apparatus described herein. Such other macromolecules include, but are not limited to, nucleic acids and oligonucleotides. Macromolecules are understood, generally, to be molecules of high molecular weight that are composed of repeating units of same or different identities. Similarly the methods of the present invention may also lead to more accurate detection of small molecules (non-macromolecules) that would otherwise be digested or degraded by other means.

The terms disrupted and degraded are used herein to refer to alteration of molecular structures in a sample. A structure is disrupted if it is altered in such a way as to impair its function, even though the structure's identity is not destroyed. Thus, a protein, for example, can be denatured and, in so doing, its secondary, and/or tertiary and/or quaternary structure is disrupted, i.e., altered such as by unraveling, so that its function is destroyed. However, such a process does not change its primary sequence and thus its identity is maintained. Conversely, a structure is degraded if its chemical identity is changed. Thus, for example, cleaving a protein to produce two or more fragments has degraded the protein because not only has its secondary and/or its tertiary and/or its quaternary structure been altered, but its primary structure has too.

The samples for use with the present invention may comprise any biological sample from an organism. Thus, the samples include, but are not limited to, tissue, muscle, bone, bone marrow, tooth, hair, skin, or any organ such as brain, kidney, liver, stomach, intestine, reproductive organs, or pancreas. The samples further include body fluids including, but not limited to tears, saliva, blood, semen, sweat, or urine.

The organism is preferably a mammal, but may be a reptile, an invertebrate, a fish, an insect, or a bird. The organism is still more preferably a human, but may be an animal, including, but not limited to: a non-human primate, rabbit, sheep, dog, cat, horse, monkey, mouse, or rat.

Exemplary Theory

While a tissue is living, proteins are synthesized and degraded. This is a dynamic process and is extensively controlled by various mechanisms. For example, proteolysis naturally occurs within living tissue but it is typically regulated so that proteins that are proteolyzed remain in sufficient quantities to perform their functions. A disease state can change this balance, and hence, a change in the balance can be used to characterize a disease.

The peptidome of a sample, the set of peptides present in a specific cell, tissue, organism or system, is directly linked to its proteome. The distribution of molecules between proteome and peptidome is controlled by proteases and protease inhibitors. Post-mortem enzyme activity plays a role in the integrity of the peptide and protein content in tissues, such as brain tissue. There is always a low level of highly abundant peptides from protein degradation in a sample that arises from the natural protein-peptide homeostasis.

Many studies of tissue and cells requires their removal from the supportive environment of a living organism, thus disturbing the various regulatory processes, and in particular leading to deprivation of oxygen and nutrients in the sample, for example as blood flow to the tissue is halted. Ischemia, a restriction on blood delivery to tissue, leads to subsequent hypoxia and anoxia.

The degradation of tissue has been particularly closely studied for samples of brain tissue. Thus, even though brain cells do not contain a reservoir of oxygen in the same way that muscle cells do, i.e., with myglobin, their rate of oxygen utilization is high. To ensure brain cell survival, a constant supply of oxygen and nutrients are required. A dilemma in the study of brain tissue is that, with many types of analytical techniques, the brain tissue must be removed from its oxygen and nutrient supplying environment. Without oxygen, oxidative phosphorylation and subsequent adenosine triphosphate ("ATP") production is halted, causing deficiencies in cell functions. The time at which degradation of brain tissue begins is much shorter than the time for degradation of other biological tissues or bodily fluids. Furthermore, even within the brain, the protein and polypeptide degradation time is not uniform. Oxygen retention is generally low and non-uniform with large variation between different brain structures. It is generally higher in the regions rich in cell bodies and dendrites, such as the grey matter of the cortex, and lower in areas where fibers predominate, such as the white matter of the cortex, pons, and fornix (see, e.g., Erecinska, et al., "Tissue Oxygen Tension and Brain Sensitivity to Hypoxia", *Respir. Physiol.*, 128, 3:263-276, (2001)).

Glucose is the main metabolic substrate for the adult brain. Glucose is metabolized through glycolysis to pyruvate, which enters the Krebs cycle in mitochondria where, in the presence of oxygen, it is completely oxidized to carbon dioxide and water (see, e.g., Goldman, et al., "Acid-induced Death in Neurons and Glia" *J. Neuroscience*, 11:2489-2497, (1991)). A decrease of oxygen interferes with the oxidation of pyruvate in the mitochondria. As a result, mitochondrial ATP production is compromised, leaving only glycolytic ATP production. In the ischemic brain, ATP generation occurs via anaerobic conversion of endogenous substances.

As noted, the brain contains only a paucity of oxygen stores. The stores of oxygen in blood vessels can support normal oxygen consumption in the brain for only a few seconds. Anaerobic glycolysis only yields 2 mol of ATP per mol of glucose, as compared to ~35 mol of ATP under aerobic glycolysis. This results in a utilization of endogenous stores of ATP, ADP and phosphocreatine (PCr). Creatine phosphate donates a phosphor group to ADP, thereby converting it to ATP. The high-energy phosphate compounds including creatine phosphate, are present in vitro in both neurons and glia at comparable concentrations. (See, e.g., Folbergrova, et al., "Phosphorylase Alpha and Labile Metabolites During Anoxia: Correlation to Membrane Fluxes of $K^+$ and $Ca^{2+}$", *J. Neurochem.*, 55(5): 1690-6, (1990)).

By using these endogenous energy substrates, energy metabolism can be supported for approximately one minute in ischemia (Hansen, A. J., "Effect of Anoxia on Ion Distribution in the Brain", *Physiol. Rev.*, 65, 1:101-48 (1985).). In ischemia studies, glucose levels are depleted and lactate levels are 3-fold increased after 60 seconds. After 2 minutes, lactate levels are increased 5-fold (Folbergrova, et al.). The utilization of high-energy phosphate groups is reduced to 30% after approximately 10 seconds, 15% after the first minute, and to nearly zero after 2 minutes (Hansen; Folbergrova, et al.).

There is an efflux of $K^+$ ions from rat brain cortex immediately after induction of anoxia through cardiac arrest (Hansen). There is a slow increase of $K^+$ ions during the first two minutes of anoxia (K-phase I). After about 2 minutes, the extracellular $K^+$ ion concentration rises from 10 mM to about 60 mM within a few seconds (K-phase II). The rapid increase in extracellular potassium takes place when the ATP energy metabolism and oxygen consumption have fallen to very low levels; between 1 and 2 minutes after ischemia. During the next few minutes the extracellular $K^+$ levels rises slowly to 80 mM (K-phase III). The slow rise during K-phase I may be due to insufficient inward pumping of $K^+$ ions due to reduced Na—K-ATPase activity. After 1 to 2 minutes of ischemia, ATP energy levels are insufficient to support Na—K-ATPase activity, causing depolarisation and a reduction of Na, K, Ca, and Cl (see, e.g., Hille, B., *Ionic Channels in Excitable Membranes*, Sinauer Associations, Sunderland, Mass., (1992)).

Complete ischemia in rat cortex induces a rapid increase in intracellular Ca levels after approximately 60 seconds (Kristian, T., "Metabolic Stages, Mitochondria and Calcium in Hypoxic/Ischemic Brain Damage", *Cell Calcium*, 36, 3-4: 221-33, (2004)). The ischemia-induced changes in ion homeostasis causes a depolarization, causing entry of Ca through voltage-dependent Ca-levels and NMDA-receptors. NMDA antagonist treatment of ischemic rat cortex delays the intracellular Ca increase within 30 seconds (Kristian). The Ca-ATPase activity and the Ca-sequestration into organelles is ATP driven by and therefore sensitive to the rate of energy metabolism. Increased glucose levels in rat cortex also delays Ca influx to 90 seconds (Kristian). When the energy metabolism is compromised, Ca is released from the organelles. The increase of Ca can activate K—Ca channels, thereby promoting K efflux (Hille). As the ion balance is lost, the cell organelles collapses and proteins and peptides are released and degraded.

As described, after removing a sample of tissue from a living organism, proteolysis increases or can continue unchecked, thereby rapidly leading to destruction of proteins and polypeptides within the sample. Therefore, to obtain the most information about the tissue's protein and polypeptide makeup, the sample should be heated as quickly as possible after removing the sample from the organism. Without being constrained to any particular theory, it is believed that the tissue should be heated prior to the ATP levels dropping below a point that ion gradients are no longer maintained in the cells in the sample. The electrochemical gradient across a cell membrane, manifested by concentration gradients of ions such as sodium and potassium, provides a source of energy for intra-cellular chemistry. Enzymes such as $Na^+$ ATPase and $K^+$ ATPase use ATP to create and maintain such gradients. Once a cell experiences energy failure, that is, once the ATP level drops below a threshold level, calcium accumulates in the intracellular space as a result of the disturbed ion homeostasis. As the ion balance is lost, the cell organelles collapses and proteins and peptides are released and degraded.

Figure 1:
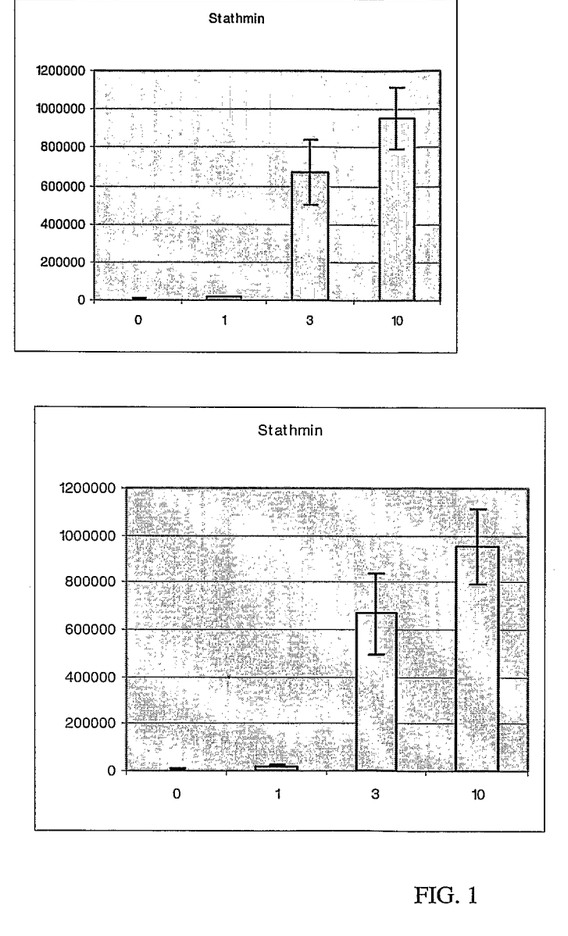
FIG. 1 shows charts of sample quality, post sampling.

The degradation of exemplary mouse brain tissue is described with respect to the changes the sample undergoes after the sample is extracted from an organism, in FIG. 1. After 15 seconds have elapsed from the time that the tissue is removed from an organism, there is about 25-50% less ATP, 50% less glucose and 50% more lactate in the tissue than in a similar sample of tissue that is still in the organism. After 45 seconds, there is about 75% less glucose and 150% more lactate. After 1 minute, there is about 50% less ATP, the pH has decreased (signifying increased acidity in the sample), the glucose is gone, there is about 200% more lactate, the sodium/potassium ATPase stops functioning, potassium depolarization occurs, and cytosolic calcium increases. After 2 minutes, there is typically no ATP remaining, there is about 350% more lactate, calcium activated protease increases and phosphorylation no longer occurs. After 3 minutes, the proteins degrade. Thereafter, necrosis (when supplies of oxygen are cut off) or apoptosis occurs. Stathmin, a 17 kDa protein, has been suggested as a marker for protein degradation. A mouse brain was analyzed for fragments of stathmin. At times between 0 and 1 minute, stathmin fragments are very low, shown as less than 5,000 units of ion intensity as detected by a mass spectrometer (***$P<0.0001$, ANOVA, t-test). After three minutes, on average, the stathmin fragments increase dramatically, which is indicated by the ion intensity of more than 600,000. After 10 minutes from extracting the sample, the stathmin fragments increase again, which is indicated by an ion intensity just under 1,000,000. Determining the degradation of stathmin is described further in "Method for Determining the Quality of a Biological Sample", U.S. Provisional Patent Application No. 60/740,542, filed Nov. 29, 2005, incorporated herein by reference.

Accordingly, in certain embodiments, an indication of sample degradation is obtained by measuring the amount of stathmin fragments in the sample, after it has been prepared by the methods described herein. If the levels of stathmin fragments are substantially higher in the sample than their corresponding levels in vivo, or if the ratio between the Stathmin protein and its degradation product is much higher than it is in vivo, i.e., if $C(Stathmin)_{in\ vivo}/C(Stathmin\ fragment)_{in\ vivo} >> C(Stathmin)_{ex\ vivo}/C(Stathmin\ fragments)_{ex\ vivo}$, then too much sample degradation has taken place. Preferably, the difference between the ratios measured in vivo and ex vivo does not exceed 50% (i.e., $Ratio_{in\ vivo}/Ratio_{ex\ vivo} < 1.5$), and still more preferably does not exceed 40%, and even more preferably does not exceed 30%, and yet more preferably does not exceed 20%, and most preferably does not exceed 10%.

For these reasons, a biological sample that is prepared using the methods described herein is denatured prior to the ion balance within the sample becoming sufficiently imbalanced (as compared to a similar sample in a living organism) that the level of molecular fragments, such as peptide fragments from proteins, found in the analyzed sample are comparable to the levels in a similar sample found in a living organism. Because ion imbalance occurs after the ATP level drops, a denatured sample may have some amount of ATP remaining.

Process

Figure 2:
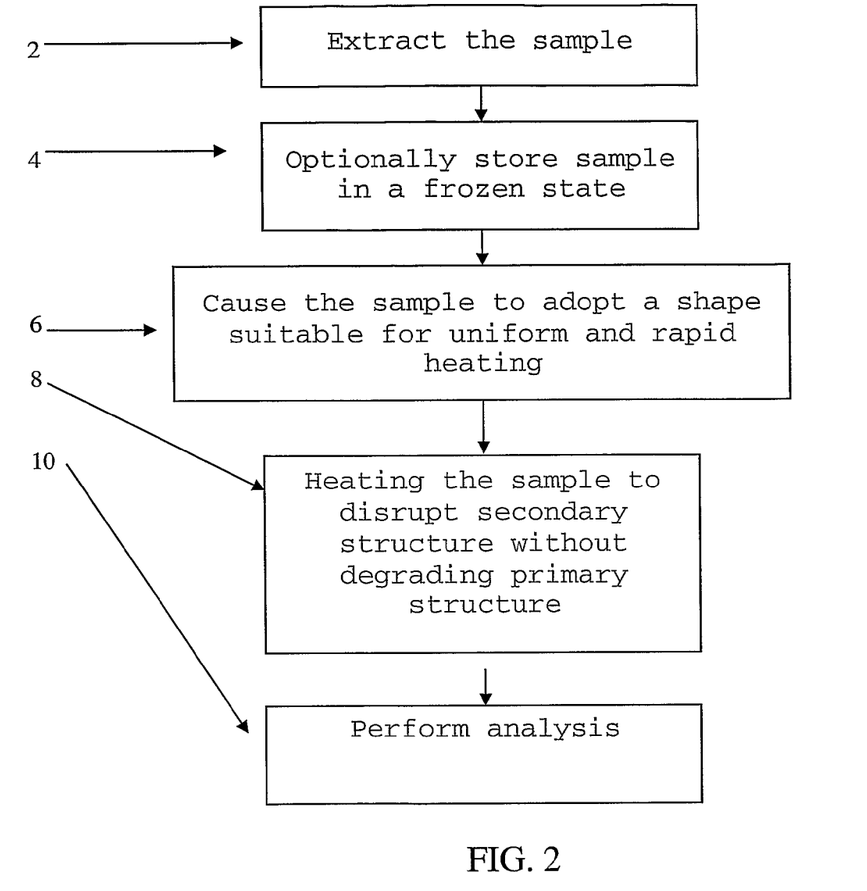
FIG. 2 shows a flow chart of a method according to the invention.

Steps of a method for preparing a biological sample for subsequent analysis according to the present invention are shown in FIG. 2. The biological sample comprises at least one protein or polypeptide, having an amino acid sequence, from an organism. The biological sample is extracted 2 from the organism. The sample is optionally frozen 4. Then, after a first period of time, the sample is caused to adopt a shape 6 such that the shape permits uniform and rapid heating. After the sample has been so shaped, the shaped sample is then heated 8 for a second period of time such that all portions of the sample are heated at relatively the same rate and achieve the same temperature at approximately the same time. Throughout the causing and heating, the sample is handled so that a minimal amount of degradation of the primary structure of the at least one polypeptide or protein occurs prior to the sample being heated. Finally, the sample may be subjected to further analysis.

Extraction

Extraction of a sample from an organism may take a number of forms. For example, the sample may be excised from the organism by cutting, taking a smear, or by drawing out with a syringe or a catheter.

While generally all biological samples undergo similar steps that eventually lead to necrosis, wherein ATP production and phosphorylation is halted, ion gradients are lost, the cell organelles collapse, proteins and peptides are released, and proteolysis increases, the rate of each of these steps depends at least in part on the type of sample. Thus, although massive degradation does not occur in some samples until as much as 10 minutes have elapsed, in some samples, massive degradation can occur as quickly as 3 minutes, 2 minutes, 1 minute, 30 seconds, 10 seconds or less from the time the tissue is removed from the organism. Accordingly, the period of time between extraction of a sample from an organism and the time that the sample is heated (as further described herein) is preferably 3 minutes, still more preferably 2 minutes, and even more preferably between 10 seconds and 2 minutes. In some embodiments, to avoid degradation of the sample, the sample can be extracted by an instrument that simultaneously removes the sample and shapes the sample into the desired shape. The sample is then immediately introduced into the heating device to arrest proteolysis.

Sample Shape

Determining how to shape the sample so that the sample can be uniformly heated preferably takes into account the type of device to be used to heat the sample, and various characteristics of the sample. The sample can be heated by one or more of the well-known forms of heat transfer: conduction, convection or radiation. If the sample is heated by conduction heating, a factor in determining how to choose the shape of the sample is that it is preferable that no part of the sample interior is greater than a threshold distance from a source of heat. Preferably this threshold is 5 mm, though it may vary with the nature of the tissue sample. For example, it may be 1 mm, 2 mm, 3 mm, 3.5 mm, 4 mm, 4.5 mm, 5.5 mm, 6 mm, 6.5 mm, 7 mm, 7.5 mm, 8 mm, 9 mm, or 1 cm. In some embodiments, it is preferable that the sample is shaped to have the largest surface area to volume ratio possible, such as by creating a very thin slice, preferably one that is uniformly thin. Where the heating device has conductive elements that are in specific shapes, such as a cylindrical heating element or a probe which is inserted into the sample, a cylindrical shape for the sample may be more desirable. The shape of the sample should be one that maximizes any temperature gradient that occurs across the sample during heating so that the heat conduction from the surface to the interior of the sample is as effective as possible. The speed of the heating step can be kept at a rate sufficiently fast, but also be selected to prevent the temperature from going too high, or from some parts of the sample from being heated too slowly and not being heated to the same temperature as the rest of the sample. If part of the sample is allowed to go beyond a maximum temperature, water in the sample may boil and the cell structure may be destroyed. In more extreme instances, the primary structure of a protein or polypeptide of interest may be destroyed by temperatures that are too high. Conversely, if part of the sample does not reach the denaturation temperature, the whole sample can be tainted by residual presence of the un-denatured portion. Uniform heating avoids both of these outcomes.

Figure 3:
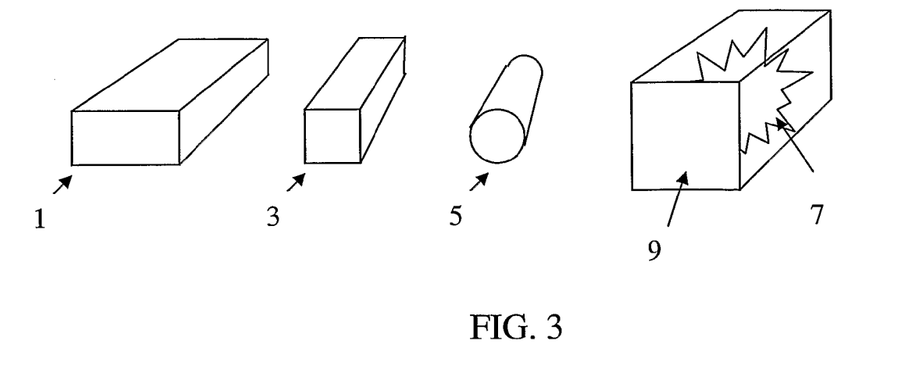
FIG. 3 shows schematics of four exemplary shapes of biological samples for use with the invention.

Referring to FIG. 3, four embodiments of shapes of biological samples suitable for use with the present invention are shown. Parallelepipeds 1, 3 and a right cylinder 5 are just a few of the possible shapes that can be uniformly heated. Other shapes, such as slices or cubes, are also suitable. Still other shapes that permit uniform and rapid heating are shapes in which heating elements—such as in the form of vanes—intersect the sample. In other embodiments, the shaped sample has at least the following attribute: its surface area to volume ratio is greater than that of a sphere of the same volume by a factor that is at least about 2, and preferably at least about 3, 5, 10, 20, or 100.

Some types of biological samples, however, are either too small to shape, or are such that valuable information could be lost if part of the sample were removed. These biological samples 7 can be introduced into a filler 9, which has a shape that allows for uniform heating of the sample, particularly when radiation heating is used. The filler 9 preferably has a similar dielectric constant and electrical conductivity as the biological sample in order to facilitate the uniform heating, and is preferably inert. In some embodiments, the filler is a fluid or a gel that includes water and salt ions. Alternatively, or in addition, for the case of heating a sample by application of microwave radiation, the filler has similar transmission characteristics with respect to electromagnetic radiation, such as its refractive indices and absorption coefficients, to those of the biological sample, which thereby prevents uneven heating of the sample.

The parallelepipeds 1, 3 and right cylinder 5 are thin and oblong in relation to their thickness, thereby facilitating rapid heat transfer in case of heat applied by contact with the sample. Examples of such heat transfer include conduction by gas, e.g., a flow of hot or warm gas directed onto the sample, condensing gas, e.g., a flow of vaporized liquid directed onto the sample, where the liquid has a low enough boiling point that the liquid is able to form condensation on sample at temperatures below, for example, 200° C., or a warm plate contacting the biological sample or contacting a container in which the biological sample is located.

The sample can be shaped by cutting the sample into the desired shape. In some embodiments, the sample is pressed, or flattened, such as by applying pressure, to achieve the desired shape. In some embodiments, the sample has a thickness of between about 1 to 2,000 microns, such as between 1 and 1,000 microns, 1 and 500 microns, 1 and 200 microns, 1 and 100 microns, 1 and 50 microns, 1 and 25 microns, 1 and 20 microns, 1 and 10 microns or 1 and 5 microns. It is to be understood that the various upper and lower endpoints of the foregoing ranges may be interchanged with one another without limitation: for example, although not specifically recited hereinabove, a range of 10-50 microns is also considered within the scope of the present invention, as is 500-1,000 microns.

It is also to be understood that the term 'about' as used herein, in connection with any quantity such as a time, or a length, or a mass, is intended to mean that the value in question may vary by up to 5% smaller or larger than the quoted value. Thus, for example, a thickness of about 10 microns is intended to mean any thickness in the range 9.5 to 10.5 microns. For temperatures, the term 'about' means that a variation of ±2° C. is intended.

The methods of the present invention can be applied to both fluid and solid samples. Samples that are solid may contain liquids within them (e.g., cells in tissues have liquid phase constituents within their cell walls), but such samples have more solid characteristics than liquid characteristics, and thus can have a definite shape and volume and need not be held by a container to maintain the shape and volume. Tissues, such as muscles, skin, brain, liver, kidney, bone, bone marrow, or others can be considered to be solid samples. Fluid samples, while possibly having components that are more solid than fluid, primarily have fluid characteristics, such as the propensity to flow and to deform when very little external force is applied. Blood, blood components, urine, semen, CSF, lymph fluid, cell extracts, saliva and tears are some of the bodily fluids that can be analyzed using the techniques described herein.

Fluid samples can be introduced into a container for retaining the sample during heating. The container has a shape that allows uniform heating of the fluid sample. In some embodiments, the fluid sample is introduced into a tube or needle. The container can also be in one of a parallelepiped, a cylinder or other suitable shape, as shown in FIG. 3. Alternatively, a flat passage or a whirl canal can be used. The sample container can also be configured for easy access to the sample after heating, as the heating can in some instances change the sample from having fluid characteristics to solid characteristics.

The sample container can be formed of a material that permits effective heat transfer through the container, such as a metal. The time for heating of the biological sample is therefore, in such instances, almost completely dependent on the heat conduction inside the sample since the heat conduction of the metal is far higher than that in the biological sample. For example, aluminium of common quality has a thermal conductivity of 190 W/mK, whereas a biological sample typically has conductivity below 1 W/mK. The sample container can also be formed of a material that does not interfere with the transfer of radiation energy into the sample, such as glass or other dielectric material or a polymer.

Unlike irradiation of a live organism where the organism is euthanized by the irradiation process, and unlike irradiation of a part of an organism such as the organism's head or its limbs, in the present invention the target sample is specifically shaped to ensure that the sample is uniformly heated and that all portions of the sample attain the desired temperature at approximately the same time. Most organisms or parts of organisms are not ideally shaped for uniform heating by irradiation or any other method of applying heat.

Freezing the Sample

Optionally, the sample can be frozen, such as by flash freezing, prior to analysis. The sample can be brought to a temperature preferably below −20° C., such as −80° C. One advantage of freezing the sample is that the sample can be manipulated and shaped into the desired shape for uniform heating more easily when the sample is in a frozen state than when fresh. Frozen samples can be cut into thickness of less than about 5 mm, about 4 mm, about 3 mm, about 2 mm, about 1 mm or 0.5 mm. Preferably, for a frozen sample, the sample shape is a thin sheet, on the order of microns thick. Such thin slices are less easily achieved when cutting a fresh sample. The freezing solidifies any liquid in the sample, including in samples considered to be solid, and allows for more precise cutting of the sample. Additionally, freezing arrests proteolytic activity and prevents degradation of other components of the sample.

When the sample is frozen after being extracted from the organism, the sample should be kept frozen, such as below −20° C. or below −4° C. prior to heating. When a sample is frozen, ice crystals form and disturb the plasma membrane. In addition, as a frozen sample thaws, vesicle membranes become permeable. Increased permeability can cause protein degradation to occur more rapidly once the sample is thawed than in samples that have never been frozen. With some types of biological samples, the sample is not permitted to thaw before applying heat to the sample. That is, the sample is not allowed come to a temperature above −20° C. before the heat is applied. If the sample is thawed, the sample is heated within about 30 seconds from the thawing of the sample, to prevent massive degradation from occurring.

Heating

After the sample has been shaped, the sample is then heated uniformly to a temperature that denatures macromolecules in the sample without degrading the primary structure of those and other macromolecules. The heating can be carried out by heat transfer from conduction, convection, or radiation. Additionally and alternatively, heating of the sample can be accomplished by directing microwave radiation on to the sample.

The sample can be heated to about 55, 60, 70, 80, 90, 95, or 100° C. at normal pressure, or the boiling point of a fluid sample, depending on the type of molecule that is to be denatured. In some embodiments, the sample is prevented from being raised over a threshold temperature, such as the boiling point of the sample, or 100° C. at normal pressure, so that the primary structure is not destroyed. The sample can be heated at a higher temperature under pressure to denature the macromolecules. Maintaining the temperature of the sample below a threshold, and thereby maintaining the macrostructure, can facilitate sample analysis. If the temperature achieved by the heating step causes the sample to reach a temperature at which the secondary structure of a macromolecule is disrupted, the macromolecule is denatured. In certain instances, the heating disables proteolytic enzymes that break other proteins and polypeptides into separate peptide fragments. The heating can arrest at least 60%, such as at least 70%, 80%, 90% or 95% of the proteolytic activity of the sample. The heating can also alter the tertiary and secondary structure of the proteins and polypeptides of interest. However, the heating does not degrade the primary structures of macromolecules, and disables other molecules within the sample that would degrade primary structure, as well.

Any of the heating devices can heat the sample rapidly, such as in less than 2 minutes, less than 1 minute, less than 30 seconds, less than 10 seconds, less than 5 seconds, less than 2 seconds, or less than 1 second. In some embodiments, the heating brings all parts of the sample to at least 60° C. within 2-3 minutes. Heating devices are described herein that work using conduction or radiation. Conduction heating can be used in instances where radiation will not heat a sample uniformly. In a sample that is frozen, using microwave radiation heating can cause some parts of the sample to attain the desired denaturation temperature before other parts of the sample. By way of analogy, a block of ice heated in the microwave will resist thawing, because the hydrogen bonded molecular network is not altered by the microwaves. For example, ice is thawed more efficiently by conduction than by applying microwave radiation. As the ice begins to melt in some areas, the melted ice, i.e., the water, begins to warm up and heats the surrounding ice by conduction. This can allow some parts of the ice block to thaw and reach boiling prior to other parts of the ice block thawing. This phenomenon in a biological sample causes uneven heating, which can allow for more peptide fragments to be present in the sample than would be present in a sample that is uniformly heated to the target temperature. One option for avoiding this is to thaw the sample prior to the heating step. Another option is to use a heating method other than microwave radiation for heating frozen samples. Such heating steps can avoid a separate thawing step altogether.

Timing

There are two phases after sample extraction from the organism in which the sample can degrade. The first phase begins at extraction and ends at the initiation of the heating step. The second phase beginning at the initiation of the heating step and ends when the sample reaches the desired temperature. If the sample is not frozen, the combination of the first and second phases should be completed prior to the sample degradation, i.e., prior to ion imbalance or depletion of ATP level and subsequent increased levels of molecular fragments in the sample. Described herein are methods for determining the time that applies for each type of biological sample. However, for a never-frozen sample it is desirable that the two phases are completed within 10 minutes, such as within 5 minutes, 3 minutes, 2 minutes, 1 minute, or 30 seconds. In some implementations, the second phase occurs within 2 minutes, 1 minute, 30 seconds, 20 seconds, 10 seconds, 5 seconds, 2 seconds, 1 second or less. The first phase can be both extended and shortened if the sample is frozen. The phase is extended, because the sample can be kept frozen for extended periods of time, such as days, weeks, months, or even years. However, the first phase is shortened in that the time between thawing the sample and heating the sample must be kept very short because of the acceleration of degradation that occurs after the sample is thawed.

Examples of Biological Analysis

After the samples are heated to a suitable temperature for denaturing the molecules, the samples can be analyzed to determine the protein and polypeptide make up of the sample. The samples can be analyzed using chromatography, mass spectroscopy, Edman degradation, or immunoassay methods such as immunostaining, immunoprecipitation, western blot, enzyme assays, or other suitable analysis methods.

Exemplary Devices

Regardless of whether the sample is fresh or frozen when heated, the sample can be placed in a container that can be evacuated so that the sample can contact a heat source directly, without a pocket of air between the sample and the heat source. The container can be a deformable piece of material, such as a bag or a foil, that does not release molecules that would interfere with analysis results. Suitable materials for such a container can include polymers, such as medical grade polymers, or other materials that do not give off gas, or have components that can migrate into the sample during sample handling.

Figure 4:
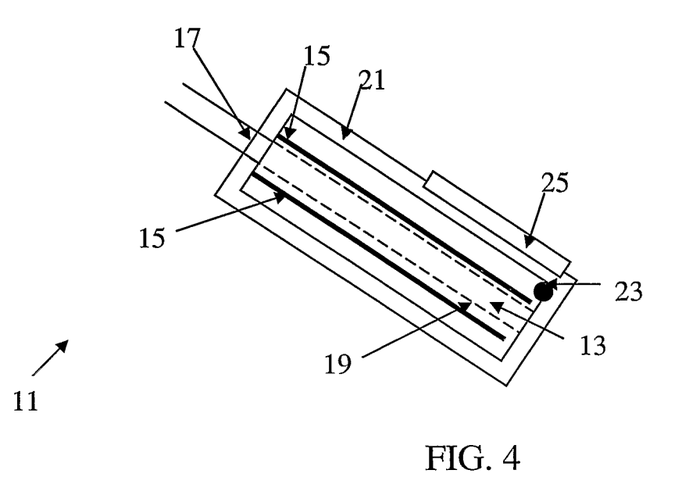
FIG. 4 is a schematic of a device for preparing a biological sample for analysis.

The prepared samples are heated in a device that is configured for uniformly heating the sample. Referring to FIG. 4, an embodiment of a heating device 11 is shown. The heating device 11 has a chamber 13 for receiving a biological sample or a container that holds the sample, and a heating element 15 for heating the sample. An opening 17 allows the biological sample (optionally in a container) to enter the chamber 13. The biological sample (optionally in a container) is introduced into the chamber 13 via the opening 17, and an inner wall 19 of the chamber 13 contacts the biological sample, or a container that holds it. The chamber 13 presents a large heat transfer surface in relation to its volume and is very close to the sample. The inner wall 19 is formed of a material that is capable of conducting heat to the sample. A thermally insulating layer 21 is provided around the chamber 13, to retain the heat within the chamber 13 and to protect objects outside of the device from being heated. A heat sensor 23 and heat controller 25 are provided for controlling the heating element 15. The heat controller 25 optionally has a timer to regulate the on time of the heating element 15, or to regulate the amount of time that heat is delivered to the sample. The device 11 can be powered by a battery or by electricity from a power supply, connected by an electrical cord (not shown). In this embodiment, the biological sample may be either fluid, for example confined to a container, or solid.

Figure 5:
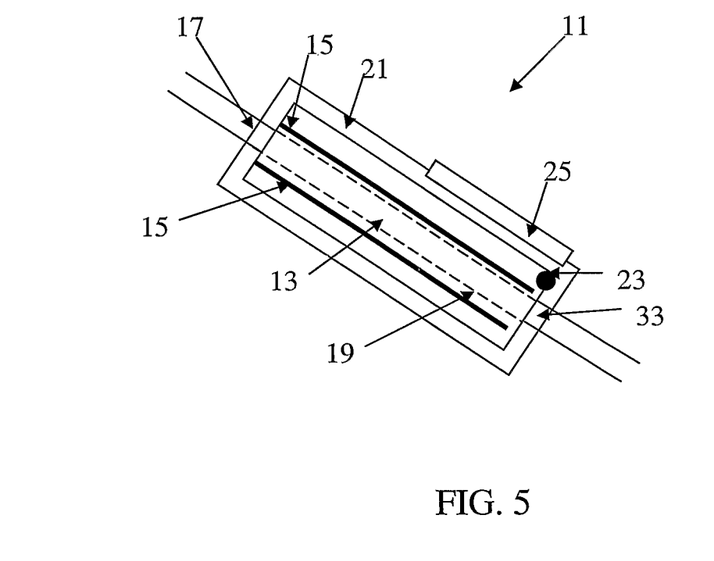
FIGS. 5-8 are schematics of devices for preparing a biological sample for analysis.

Referring to FIG. 5, another embodiment of a device 11 is configured for allowing the sample to enter and exit through separate openings. The same reference numerals are used in FIGS. 4 and 5 to refer to the same features. Device 11 in FIG. 5 has a second opening 33 to allow a fluid biological sample to flow out of the chamber 13. A biological sample that can be used with the heating device of FIG. 5 is preferably a fluid which is non-coagulating. The biological sample is physically shaped as it is introduced into the chamber 13. In this embodiment, the cross section of the chamber 13 is designed so that it presents a wide base and a low height, with the intention of a fast and uniform heat transfer through the whole biological sample.

Figure 6:
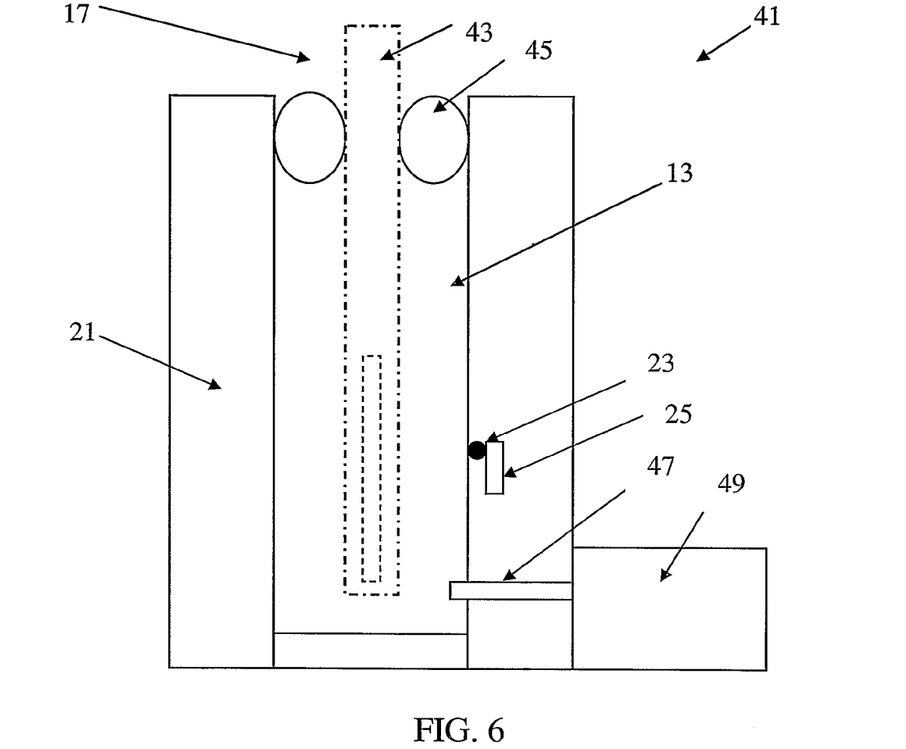

FIG. 6 shows an alternative embodiment of a device 41, configured for use with a sample that is introduced into the heating chamber in a container. The biological sample in a container 43, such as a tube or a needle, is introduced into a chamber 13 via the opening 17. The opening 17 has an O-ring 45 (shown in cross-section in FIG. 6), which seals the container 43 into the chamber 13. The chamber 13 and the container 43 are sized so that the container 43 does not contact all of the walls of the chamber 13, and in some embodiments, the container 43 contacts nothing other than the O-ring 45. This arrangement provides a space in which steam can be introduced for heating the sample. A steam generator 49 communicates with the chamber 13 through a steam inlet 47. The chamber 13 optionally includes a steam pressure control (not shown). As steam enters the chamber 13, the container 43 and the biological sample within it (not shown) are heated. In some embodiments, the steam is replaced by another heated fluid.

Figure 7:
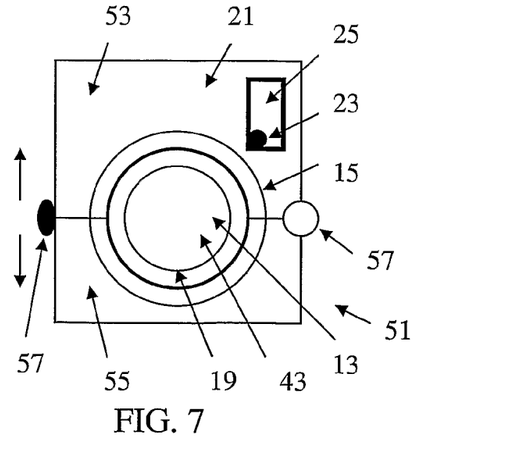

Referring to FIG. 7, a plan view of a heating device 51 in which samples in a container can be introduced is shown. The device's chamber 13 comprises two moveable matching parts 53, 55 and a locking means 57 for maintaining the two matching parts 53, 55 in a locked state. The two moveable matching parts 53, 55 can rotate apart, such as by rotating around hinge 57. The device 51 according to this embodiment is opened and closed as indicated by the arrows. Alternatively, the moveable parts can slide open along a track. A biological sample in a container 43, such as a tube or a needle, is put into the chamber 13 when the moveable matching parts 53, 55 are moved so that the device is open. After closing and locking the two matching parts 53, 55, the heating control means 25 is activated. Alternatively, the heating control means 25 is activated prior to introducing the sample into the heating device 51. A thermally insulating layer 21 is provided around the chamber 13. An inner wall 19 of the chamber 13 is in contact with the container 43. This allows fast and uniform heat transfer through the whole biological sample. Although the device 51 is shown with two moveable pieces, other numbers of moveable pieces can be incorporated into the device, consistent with the foregoing description.

In some embodiments, the heat source is a single plate heated, e.g., by a heating element, and the sample, regardless of whether it is placed in a container, receives heat from one side only, i.e., there is a single contact surface allowing power to be transferred into the biological sample.

Figure 8:
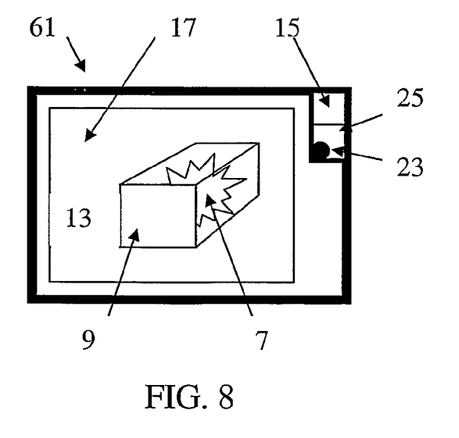

Referring to FIG. 8, a device 61 that uses radiation (e.g., microwave radiation) to heat the biological sample is shown. The device 61 comprises a chamber 13 for receiving the biological sample 7. The source of radiation 15 can be a microwave generator. Alternatively, other types of radiation can be applied to the sample, such as radiofrequency (RF) or ultrasound. This embodiment also comprises an opening 17, which can be covered by a door, for allowing the biological sample 7 to enter the chamber 13. The biological sample 7 is introduced into the chamber 13 via the opening 17. A heat sensor 23 and heat controller 25 are provided for controlling the heater 15. The source of radiation can output about 1 to 6 Watts of energy, such as between about 3 and 5 watts. In some embodiments, between about 2 and 4 Watts/minute/gram, such as 3.6 Watts*minute, are input into the sample to raise the temperature of the sample from 20 to 80 degrees, if the biological sample has a thermal capacity similar to water. The needed radiation energy is 3.6/efficiency Watts*minutes/gram., i.e., if the efficiency is 10%, the needed radiation is 36 Watts*minutes/gram. The mass includes both the sample and the filler, i.e., if the filler has a similar mass to the sample and the sample weighs 10 grams, with an efficiency of 10% then 360 Watts are needed to heat the sample to 80 degrees in one minute. Thus, about 72 Watts are required to heat one gram at 20° C. to 80° C. in 30 seconds.

The chambers described in any of the devices mentioned herein can have other shapes including, but not limited to, a rectangular, square, circular, oval or triangular cross section.

Figure 9:
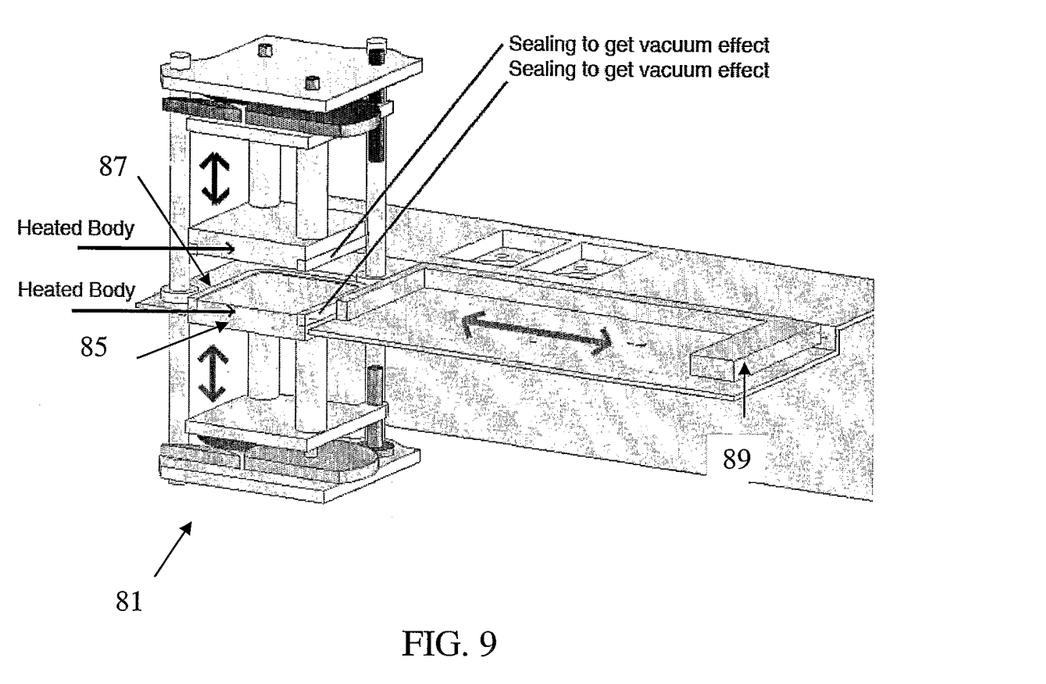
FIG. 9 is a perspective view of a device for preparing a biological sample for analysis.

Referring to FIG. 9, a device for conductively heating a sample is shown. The device 81 has two retaining members 85 that are capable of conducting heat from one or more respective heat sources. In some embodiments, the retaining members are formed of a material having high thermal conductivity, such as a metal. It need not be necessary to continually supply heat to the retaining members; this is particularly so if the members are sufficiently large that the temperature does not drop on the plates by more than 10° C. when the sample is added. In some embodiments, the members 85 have a layer of gel or oil that is heated and covered by a protecting layer, such as a plastic. The gel or oil is deformable and is able to contact all parts of the biological sample during heating. Optionally, the members have a recessed area for retaining the sample. The members can completely surround the sample. A seal 87 can be provided around the recessed area on the members 85 in which the sample is placed, so that when the members are brought together, a vacuum can be applied to the sample to eliminate air pockets between the sample and the members 85. The vacuum can be applied by a vacuum pump (not shown). In one embodiment, to create a vacuum, a lumen (not shown) is formed between the sample holding portion of at least one member 85 and a vacuum source. The members are connected to an energy source, such as electricity, so that the members can be heated. The members can have substantial mass in comparison to the sample so that when the sample is placed on the members, a negligible change in temperature is experienced by the members 85.

During operation of device 81, the sample can be protected from the members by a layer of material that can endure heating, but which does not release volatile molecules when heated, such as silicone, polycarbonate or PTFE (e.g., TEFLON™). A sensor can sense the temperature of the members 85 and ensure that the temperature does not become too high. The sensor can be an IR camera or a thermocouple or other suitable sensor. The sensor, or sensors, can be connected to one or both of the members 85. The members 85 can be moved closer together and further apart (in the directions of arrows) to allow for loading and retrieving of the sample. Optionally, a transfer element 89 can be used to load and retrieve the sample. The transfer element 89 can be within a chilled environment. In some embodiments, the chilled environment is defined by a housing (not shown) surrounding a portion of the device 81. A source of chilled air can be supplied within the housing to maintain a desired temperature. In some embodiments, the transfer element 89 and apparatus surrounding the transfer element 89 are themselves chilled, such as by a source of chilled fluid. The chilled element 89 and/or environment can maintain the sample in a frozen state, preferably below −20° C., prior to heating.

EXAMPLE 1

Analysis of Mouse Brain Samples

Twelve mice (C57/BL6) were euthanized by cervical dislocation. The twelve mice were divided into three groups and each mouse brain was kept at room temperature (22° C.) for 1, 3, or 10 minutes. At their respective time point, the mouse brains were irradiated in a small animal microwave for 1.4 seconds at 4.5-5 kW. A fourth group was euthanized by focused microwave irradiation (the control group). The striatum, hypothalamus and cortex were thereafter rapidly dissected out of all of the mice after microwave radiation and stored at −80° C.

An additional group of four mice were also euthanized by cervical dislocation and the mouse heads were immediately cooled in liquid nitrogen. The striatum was rapidly dissected out on dry ice and frozen at −80° C. The frozen samples were shaped into thin slices. Half of the group of samples were then immediately heated to near 100° C. using a contact heating device. The other half of the samples were thawed and prepared at 4° C.

The brain tissues were then suspended in cold extraction solution (0.25% acetic acid) and homogenized by microtip sonication (Vibra cell 750, Sonics & Materials Inc., Newtown, Conn.) to a concentration of 0.2 mg tissue/µL. The suspension was centrifuged at 20,000 g for 30 min at 4° C. The protein- and peptide-containing supernatant was transferred to a centrifugal filter device (Microcon YM-10, Millipore, Bedford, Mass.) with a nominal molecular weight limit of 10,000 Da, and centrifuged at 14,000 g for 45 min at 4° C. Finally, the peptide filtrate was frozen and stored at −80° C. until analysis.

The samples were then analyzed, by monitoring phosphorylated proteins; by phosphor-specific western blotting and by qualitative and quantitative peptide analysis, using nanoLC/ESI MS.

The samples that were allowed to remain at room temperature after cervical dislocation were compared to the control group. The control group displayed an average of 660±70 distinct MS peaks from striatum using nanoLC ESI MS. Within one minute post mortem, protein fragments from degrading proteins were detected, and the peptides increased to 1060±400 peaks. Three minutes post mortem the number peptides reached 2150±800 and after 10 minutes, the number of peptides reached 2800±500.

The samples that were in vitro inactivated on snap frozen samples were compared to non-inactivated samples (non-heated samples) and the control samples. In the samples that were merely frozen, allowed to thaw to 4° C. and prepared, a large number of peptides were detected. The samples that were heat treated immediately after being dissected on ice demonstrated peptide identities analogous to the control results.

The techniques described herein can offer a number of advantages. Low abundance peptides, such as neuropeptides, remain intact for analysis, proteolytic degradation of proteins is minimized and post-translational modifications of the neuropeptides are conserved. The samples can be fixed without the use of fixing solutions, such as aldehydes. When samples free of fixation solution are analyzed, there are fewer impurities that must be factored out from the data. While fixing solutions can maintain the physical shape of tissues, the fixing solution can change the molecules. The heating process is able to fix the samples and maintain information that is lost when a fixing solution is used. The techniques described herein allow the samples to be analyzed for detection of abnormalities, such as disease markers. Additionally, autopsy samples, bio bank samples, biopsy samples and other samples that are not suitable for in vivo inactivation or denaturation can be sampled without loss of polypeptide information. Samples removed at a clinic and frozen can be subsequently analyzed using technique described herein to diagnose diseases or abnormalities.

The foregoing description is intended to illustrate various aspects of the present invention. It is not intended that the examples presented herein limit the scope of the present invention. The invention now being fully described, it will be apparent to one of ordinary skill in the art that many changes and modifications can be made thereto without departing from the spirit or scope of the appended claims.

All publications referred to herein are hereby incorporated by reference for all purposes.

What is claimed is:

1. An apparatus for preparing a biological sample, the apparatus comprising;
   a retaining member;
   a sample chamber;
   one or more heating elements;
   a transfer element;
   a sealing element; and
   a vacuum pump,
   wherein
      the retaining member comprises the sample chamber;
      the sample chamber is configured to comprise a biological sample;
      the one or more heating elements are in communication with the retaining member such that heat can be transferred by conduction, convection, or radiation to a biological sample when present in the sample chamber of the retaining member;
      the transfer element is fixably positioned adjacent to or on the retaining member and movable toward and away from the sample chamber such that the transfer element can introduce a biological sample into the sample chamber and the transfer element can remove a biological sample from the sample chamber;
      the sealing element configured to create a seal around the retaining member when the biological sample is heated; and
      the retaining member and the sealing element together form a cavity that is in communication with the pump.

2. The apparatus of claim 1 further comprising:
   a heat sensor and
   an inlet,
   wherein
      the sample chamber is configured to receive and totally contain a shaped biological sample;
      the sample chamber has one or more internal surfaces;
      the one or more internal surfaces of the sample chamber are in contact with the shaped biological sample;
      the one or more heating elements are in communication with the one or more internal surfaces of the sample chamber;
      the heat sensor is in communication with the one or more internal surfaces of the sample chamber;
      the inlet is adapted to permit the shaped biological sample to be directed into the chamber by the transfer element; and
      the sample chamber has a shape so that no part of the biological sample is greater than 10 mm from a point on any one or more internal surfaces.

3. The apparatus of claim 2, wherein the sample chamber is configured to receive and totally contain a shaped biological sample having a surface area to volume ratio of about two times or greater than that of a sphere.

4. The apparatus of claim 1, wherein the heating element uses radiation to heat the sample.

5. The apparatus of claim 1, wherein the heating element uses condition to heat the sample.

6. An apparatus for preparing a biological sample, the apparatus comprising:
   a retaining member;
   a sample chamber;
   one or more heating elements; and
   a transfer element,
   wherein
      the retaining member comprises the sample chamber;
      the sample chamber is configured to comprise a biological sample;
      the one or more heating elements are in communication with the retaining member such that heat can be transferred by microwave radiation, radiofrequency radiation, or ultrasound; and
      the transfer element is fixably positioned adjacent to or on the retaining member and movable towards and away from the sample chamber such that the transfer element can introduce a biological sample into the sample chamber and the transfer element can remove a biological sample from the sample chamber.

7. An apparatus for preparing a biological sample, the apparatus comprising:
   a first retaining member and a second retaining member, both the first retaining member and the second retaining member capable of conducting heat from one or more heat sources;
   a sample chamber;
   one or more heating elements; and
   a transfer element,
   wherein
      the first retaining member is releasably attached to the second retaining member so as to allow an open configuration and a closed configuration;
      the closed configuration of the first retaining member and the second retaining member forms the sample chamber;
      the sample chamber is configured to comprise a biological sample;
      the one or more heating elements are in communication with the retaining member such that the heat can be transferred by conduction, convection, or radiation to a biological sample when present in the sample chamber; and
      the transfer element is fixably positioned adjacent to or on the first retaining member or the second retaining member and movable towards and away from the sample chamber such that the transfer element can introduce a biological sample into the sample chamber and the transfer element can remove a biological sample from the sample chamber.

8. An apparatus for preparing a biological sample, the apparatus comprising:
   a retaining member;
   a sample chamber;
   a sample container;
   one or more heating elements; and
   a transfer element,
   wherein
      the sample container comprises a deformable thermally conductive material,
      the sample container is configured to comprise a biological sample,
      the sample chamber is configured to comprise the sample container,
      the transfer element is operably linked to the retaining member such that the transfer element can introduce the sample container comprising a biological sample into the sample chamber and the transfer element can remove the sample container comprising a biological sample from the sample chamber;
      the retaining member comprises the sample chamber;
      the one or more heating elements are in communication with the retaining member such that heat can be transferred by conduction, convection, or radiation to a biological sample when present in the container; and
      the transfer element is fixably positioned adjacent to or on the retaining member and movable towards and away from the sample chamber such that the transfer element can introduce a biological sample into the sample chamber and the transfer element can remove a biological sample from the sample chamber.

9. The apparatus of claim 8, wherein the sample container is in contact with an inner wall of the retaining member when inside the sample chamber.

10. The apparatus of claim 8, wherein the sample container can be evacuated such that there is no air pocket between any of the heat element, retaining member, sample container, and a biological sample within the sample container.

* * * * *